(12) United States Patent
Tully et al.

(10) Patent No.: US 8,333,745 B2
(45) Date of Patent: Dec. 18, 2012

(54) ADJUSTABLE DRAIN LOOP FOR URINE COLLECTION SYSTEM

(75) Inventors: Stephen Tully, Cambridge, MA (US); Lawrence Salvadori, San Diego, CA (US)

(73) Assignee: Covidien LP, Mansfield, MA (US)

( * ) Notice: Subject to any disclaimer, the term of this patent is extended or adjusted under 35 U.S.C. 154(b) by 786 days.

(21) Appl. No.: 12/274,936

(22) Filed: Nov. 20, 2008

(65) Prior Publication Data

US 2009/0082742 A1    Mar. 26, 2009

Related U.S. Application Data

(62) Division of application No. 11/401,543, filed on Apr. 11, 2006, now abandoned.

(51) Int. Cl.
*A61M 1/00*    (2006.01)
(52) U.S. Cl. .................................. 604/322; 248/229.16
(58) Field of Classification Search .................. 604/180, 604/317, 319, 322, 540, 544; 248/229.16
See application file for complete search history.

(56) References Cited

U.S. PATENT DOCUMENTS

| | | |
|---|---|---|
| 2,758,477 A | 7/1953 | Mains |
| 2,759,477 A | 8/1956 | Mains |
| 3,251,069 A | 5/1966 | Clark |
| 3,259,920 A | 7/1966 | Voller |
| 3,503,401 A | 3/1970 | Anderson et al. |
| 3,534,738 A | 10/1970 | Huck |
| 3,537,109 A | 11/1970 | Spurrier et al. |
| 3,598,124 A | 8/1971 | Andersen et al. |
| 3,661,143 A | 5/1972 | Henkin |
| 3,690,315 A | 9/1972 | Chittenden et al. |
| 3,831,453 A | 8/1974 | McWhorter |
| 3,906,935 A | 9/1975 | Raia et al. |
| 4,015,605 A | 4/1977 | Mcwhorter |
| 4,019,707 A | 4/1977 | Quinn et al. |
| 4,027,842 A | 6/1977 | Mittleman |
| 4,057,062 A | 11/1977 | Lavigne |
| 4,095,589 A | 6/1978 | Manschot et al. |
| 4,189,789 A | 2/1980 | Hofstetter |
| 4,192,295 A | 3/1980 | Sherlock |
| 4,219,177 A | 8/1980 | O'Day |
| 4,254,771 A | 3/1981 | Vidal |
| 4,265,243 A | 5/1981 | Taylor |

(Continued)

FOREIGN PATENT DOCUMENTS

DE    199 59 965    6/2000

(Continued)

OTHER PUBLICATIONS

Official Action issued in Chinese Patent Appln. No. 200710096530.0 in U.S. Appl. No. 11/401,543, filed Apr. 11, 2006.

(Continued)

*Primary Examiner* — Melanie Hand
(74) *Attorney, Agent, or Firm* — Lisa E. Winsor, Esq.

(57) ABSTRACT

Disclosed is a device for maintaining an adjustable loop in the drain tube of a urine collection and/or monitoring system. The clip, band or bands act to maintain the adjustable loop such that the adjustment in size of the loop created in the drain tube varies the effective length of the drain tube. Further disclosed is a method for preventing back pressure from developing in the drain tube of urine collection and/or monitoring system.

6 Claims, 10 Drawing Sheets

U.S. PATENT DOCUMENTS

| | | | |
|---|---|---|---|
| 4,312,352 A | 1/1982 | Meisch et al. | |
| 4,317,550 A | 3/1982 | Hannah | |
| 4,332,252 A | 6/1982 | Taylor | |
| 4,393,880 A | 7/1983 | Taylor | |
| 4,417,892 A | 11/1983 | Meisch | |
| 4,421,509 A | 12/1983 | Schneider et al. | |
| 4,449,969 A | 5/1984 | Schweizer | |
| 4,452,253 A | 6/1984 | Peterson et al. | |
| 4,460,362 A | 7/1984 | Bates | |
| 4,465,484 A | 8/1984 | Cianci | |
| 4,475,907 A | 10/1984 | Voges | |
| 1,534,766 A | 8/1985 | Steer at al. | |
| 4,551,141 A | 11/1985 | McNeil | |
| 4,562,984 A | 1/1986 | Sherlock et al. | |
| 4,581,763 A | 4/1986 | Olsen | |
| 4,606,736 A | 8/1986 | Van DeWeghe | |
| 4,625,734 A | 12/1986 | Sherlock et al. | |
| 4,650,478 A | 3/1987 | Dunn | |
| 4,658,834 A | 4/1987 | Blankenship et al. | |
| 4,659,329 A | 4/1987 | Annis | |
| 4,707,906 A | 11/1987 | Posey | |
| 4,717,388 A | 1/1988 | Steer et al. | |
| 4,731,062 A | 3/1988 | Gross et al. | |
| 4,865,046 A | 9/1989 | Duran | |
| 4,972,844 A | 11/1990 | Cianci et al. | |
| 4,997,426 A | 3/1991 | Dingeman et al. | |
| 5,037,397 A * | 8/1991 | Kalt et al. | 604/174 |
| 5,207,661 A | 5/1993 | Repschlager | |
| 5,211,642 A | 5/1993 | Clendenning | |
| 5,254,110 A | 10/1993 | Marcus et al. | |
| 5,309,604 A | 5/1994 | Poulsen | |
| 5,375,799 A | 12/1994 | Rhodes | |
| 5,417,657 A | 5/1995 | Haver | |
| 5,429,623 A | 7/1995 | Dessel | |
| 5,725,515 A | 3/1998 | Propp | |
| 5,871,189 A * | 2/1999 | Hoftman | 248/229.16 |
| 5,891,051 A | 4/1999 | Han et al. | |
| 5,919,146 A | 7/1999 | Propp | |
| 6,105,218 A | 8/2000 | Reekie | |
| 6,129,714 A | 10/2000 | Kocsi | |
| 6,132,407 A | 10/2000 | Genese et al. | |
| 6,405,414 B1 | 6/2002 | Byrnes et al. | |
| 6,447,492 B1 | 9/2002 | Frohn | |
| 6,736,803 B2 | 5/2004 | Cawood | |
| 6,857,137 B2 | 2/2005 | Otto | |
| 2006/0271019 A1 * | 11/2006 | Stoller et al. | 604/544 |

FOREIGN PATENT DOCUMENTS

| | | |
|---|---|---|
| DE | 20318261 | 3/2004 |
| DE | 20318261 U1 | 3/2004 |
| DE | 20318261 U | 4/2004 |
| WO | WO 2005/051462 A1 | 6/2005 |
| WO | WO 2005/051472 | 6/2005 |
| WO | WO 2005/051472 A | 6/2005 |
| WO | WO 2006/026290 | 3/2006 |
| WO | WO 2006/026290 A | 3/2006 |
| WO | WO 2006/026290 A2 | 3/2006 |
| WO | WO 2006/044621 | 4/2006 |
| WO | WO 2006/044621 A2 | 4/2006 |
| WO | WO 2007/104350 A1 | 9/2007 |

OTHER PUBLICATIONS

Chinese Official Action (English Translation) dated Dec. 21, 2010 issued in co-pending Chinese Patent Application No. 20071009653.0
European Search Report mailed Dec. 2, 2010 issued in co-pending EP Application No. 10 177 539.3.
Communication from Examining Division issued in EP 10 177 539. 3-2310.
Official Action issued in Chinese Patent Appln. No. 200710096530. 0.

* cited by examiner

ADJUSTABLE DRAIN LOOP FOR URINE COLLECTION SYSTEM

CROSS REFERENCE TO RELATED APPLICATIONS

This application is a divisional application of application Ser. No. 11/401,543, filed Apr. 11, 2006, the disclosure of which is hereby incorporated by reference in its entirety.

BACKGROUND

1. Technical Field

The present disclosure relates to urine collection and/or monitoring systems and, more particularly, to a device for forming an adjustable drain tube loop for use with urine collection systems.

2. Background of Related Art

Urine collection and/or monitoring systems are well known and are commonly used to collect urine from a catheterized patient. Urine collection systems consist of a catheter operably connected to a patient, a fluid reservoir for collecting the fluid and a drain tube connecting the catheter with the reservoir. Typically, urine collection system are employed prior to, during and following many surgical procedures, especially where the patient is not ambulatory or is not coherent enough to negotiate the facilities normally.

It is desirable in urine collection systems to provide a drain tube that is longer then necessary to connect the catheter with the fluid reservoir. The extra length in the drain tube permits the repositioning of the patient without stressing the catheter and fluid reservoir connections, an occurrence which can cause great pain for the patient. A patient may need to be repositioned countless times during a hospital stay, including when the bed sheets have been soiled and necessitate changing, when certain tests are performed, and to prevent atrophy of the patient's muscles. Drain tubes are manufactured in standard lengths with sufficient excess tubing to allow for repositioning of the attached patient. Fasteners positioned on each end of a standard drain tubes prevents the tubes themselves from being shortened.

The excess length in the drain tube, however, often causes problems with urine flow. Urine meters and fluid reservoirs are generally secured to the bed frame or bed rail near the patient. The drain tube originates at the catheter end connected to a patient positioned horizontally in the bed. The drain tube may hang off the edge of the bed and fall below the frame of the bed before returning uphill to empty into the fluid reservoir (FIG. 1). This drain tube configuration forces urine to flow against gravity and creates back pressure on the patient's bladder. The 4-8" of urodynamic resting bladder pressure produced by the bladder of a supine patient cannot overcome this back pressure. This back pressure can restrict urine flow and potentially cause patient discomfort, bladder distension, leakage, etc.

Therefore, it would be beneficial to have a device for forming an adjustable length drain tube for urine collection and/or monitoring systems such that the length of the tube can be adjusted while maintaining the entire length of drain tube above the fluid reservoir.

SUMMARY

In accordance with the present disclosure, a clip is provided for forming a selectively adjustable loop in a drain tube. In one embodiment, the clip includes a base and at least one pair of arms extending from the base. The arms form an inner gripping surface configured to adjustably retain at least a first section of a drain tube in an adjacent relationship to a second section of the drain tube. The clip may also include a means for fastening the clip to a bed or bed sheets, e.g., a fastener loop, a safety pin, a secondary clip, etc.

In another embodiment, a device for maintaining an adjustable loop in a drain tube of a urine collection system is disclosed which includes a base defining at least one recess for retaining first and second sections of a drain tube in an adjacent relationship to one another. The device may include a means for fastening the device to a bed or bed sheets. The base may define two recesses for slidably retaining the first and second sections of the drain tube in adjacent relationship to one another.

In another embodiment, a drain tube for use with a urine collection system is provided which includes a tube forming a loop wherein two sections of the tube are in an adjacent relationship to one another and a retaining device configured to adjustably retain the two sections of the tube in adjacent relationship to one another. The device is selected from the group consisting of a clip, band, or multiple bands. The device may also include a means for fastening the loop to a bed or bed sheets. The means for fastening the loop can be formed integral with the retaining device.

In another embodiment, a method of preventing back pressure from forming in a drain tube of a urine collection and/or monitoring system is provided which includes the steps of providing a drain tube having an adjustable loop formed therein, and positioning the adjustable loop horizontally above an inlet to the urine collection and/or monitoring system.

DETAILED DESCRIPTION OF THE DRAWINGS

Embodiments of the presently disclosed adjustable drain tube loop for a urine collection system will now be described in detail with reference to the drawings wherein like reference numerals designate identical or corresponding elements in each of the several views.

Figure 1:
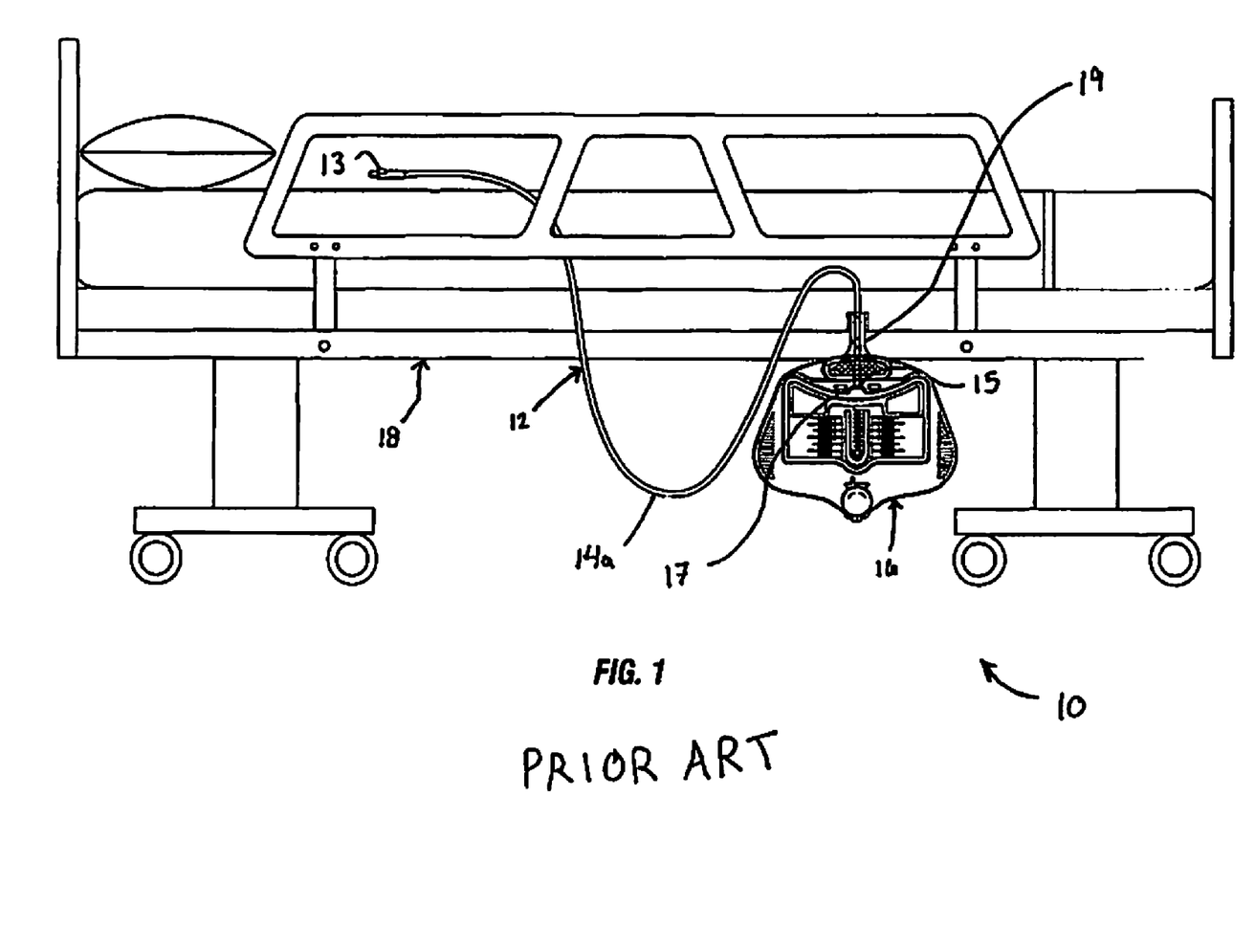
FIG. 1 is a side view of a urine collection system, including a urine collection device affixed to the frame of a hospital bed and employing the conventional practice of hanging the tube below the collection reservoir.

FIG. 1 illustrates a urine collection system 10 having a drain tube 12 and a fluid reservoir, and/or urine meter 16. Drain tube 12 includes a catheter end 13 and a connection end 15. Catheter end 13 of drain tube 12 is configured to operably connect with a catheter (not shown) attached to or positioned within a patient. Connection end 15 is configured to operably connect to port 17 of fluid reservoir 16. Port 17 is positioned on the top of reservoir 16. Fluid reservoir 16 is secured to bed frame 18 by support 19 in a location corresponding to the position of the patient. As is customary with drain tubes used in association with urine collection systems, drain tube 12 is longer than would be sufficient to connect a patient positioned horizontally in the bed with fluid reservoir 16. Urine collection system 10 employs the conventional practice of allowing the excess slack 14a in drain tube 12 to fall below the port 17 of fluid reservoir 16. In this configuration, as urine is drained through drain tube 12 into fluid reservoir 16 the urine must travel uphill to empty into fluid reservoir 16 through port 17. A back pressure results from the urine having to travel against gravity in order to empty into reservoir 16. The resulting back pressure can lead to serious complications including patient discomfort, bladder distension, and meatal leakage.

Figure 2:
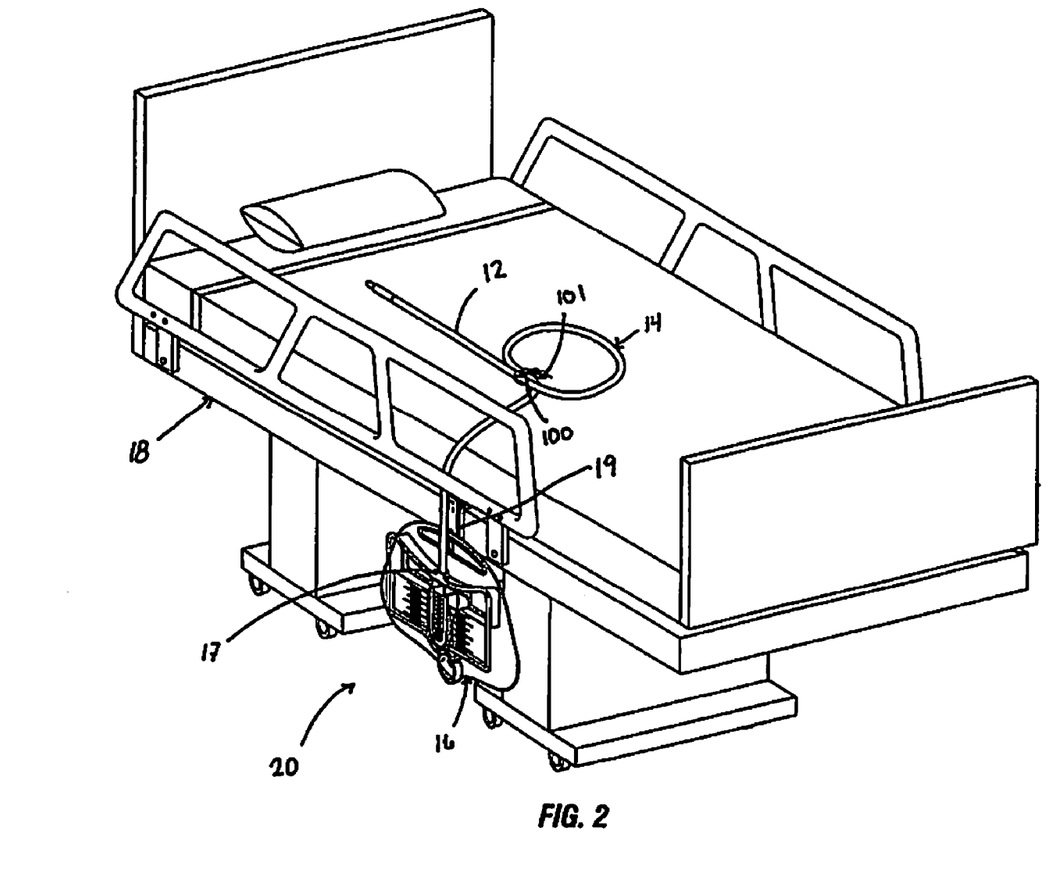
FIG. 2 is perspective view of a urine collection system, including a urine collection device affixed to the frame of a hospital bed and a drain tube configured with a clip constructed in accordance with the present disclosure.
Figure 3:
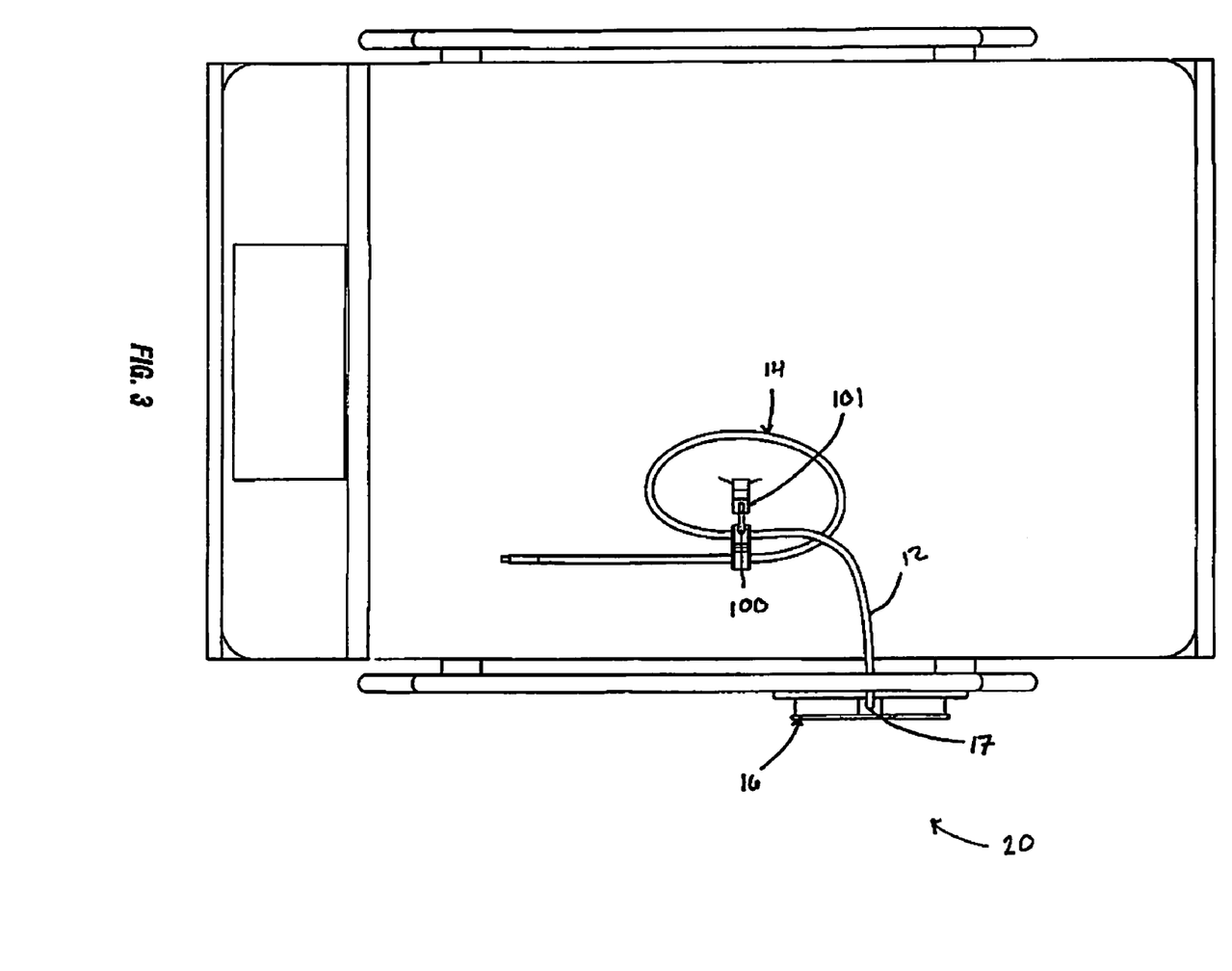
FIG. 3 is a top view of the urine collection system of FIG. 2.

Referring now to FIGS. 2 and 3, illustrated is urine collection system 20 employing an adjustable drain tube loop constructed in accordance the present disclosure. Like the conventional urine collection system practice illustrated in FIG. 1, fluid reservoir, and/or urine meter, 16 is suspended from the bed frame 18 by support 19. Unlike the conventional drainage practice of allowing drain tube 12 to fall below port 17 of fluid reservoir 16, drain tube 12 in urine collection system 20 is entirely maintained above port 17 of fluid reservoir 16. An adjustable loop 14 is formed in drain tube 12 with the configuration being maintained by clip 100. The effective length of drain tube 12, that is, the length of drain tube 12 between catheter end 13 and connection end 15, excluding adjustable loop 14, can be adjusted by varying the size of adjustable loop 14. Adjustable loop 14 permits the excess length of drain tube 12 to lay substantially flat on the bed, above port 17 of fluid reservoir 16. In this manner, the entire length of drain tube 12 is prevented from falling below entrance port 17 of fluid reservoir 16. This configuration alleviates or minimizes the back pressure created in drain tube 12 which occurs when employing the conventional practice of allowing drain tube 12 to hang below entrance port 17 of fluid reservoir 16. Sheet clip 101 is affixed to clip 100 and secures adjustable loop 14 to the bed.

Figure 4:
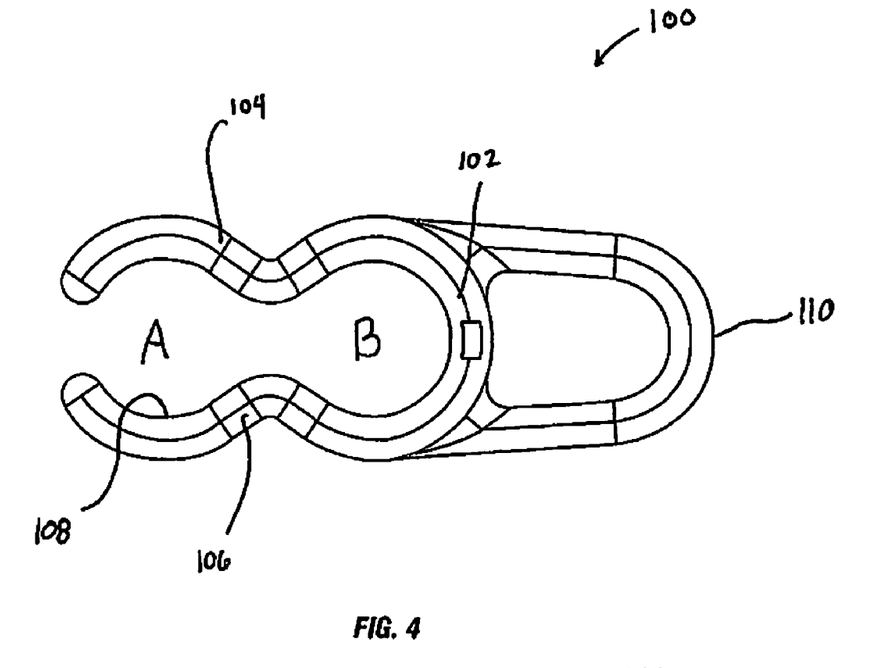
FIG. 4 is a side view of one embodiment of a clip constructed in accordance with the present disclosure.
Figure 5:
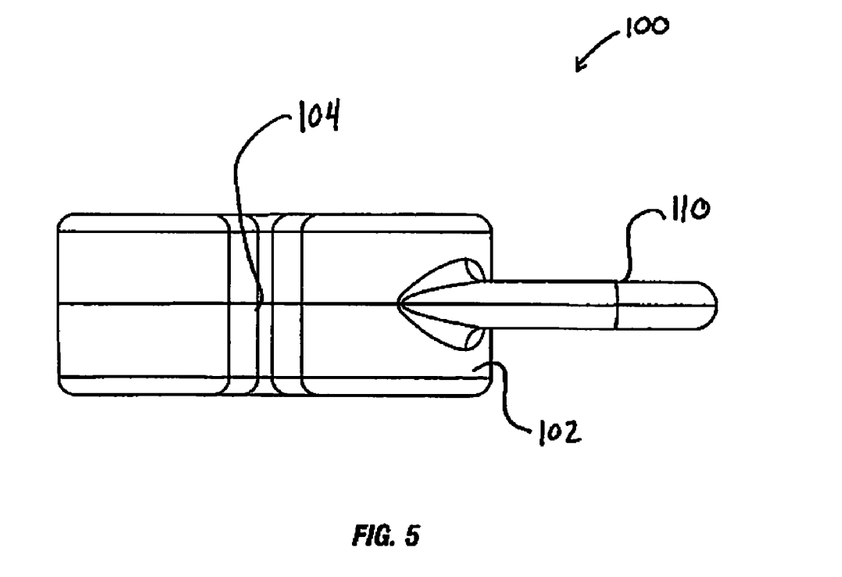
FIG. 5 is a top view of the embodiment shown in FIG. 5.

FIGS. 4 and 5 illustrate one embodiment of the presently disclosed adjustable loop clip shown generally as 100. Clip 100 is constructed as an integrally molded one-piece plastic clip or connector, which can be formed from metal, plastic, or the like. Clip 100 includes base 102, longitudinally opposed arms 104 and 106 extending from base 102, and fastener hoop 110, also extending from base 102. Opposed arms 104, 106 are constructed and dimensioned to resiliently engage, grip and hold adjacent sections of drain tube 12 in juxtaposed or adjacent relationship to one another. Each of the opposed arms 104, 106 extend from base 102 in a mirror image relationship to one another to form an inner gripping surface 108. Gripping surface 108 defines recesses A and B configured for receiving different sections of drain tube 12.

Figure 6:
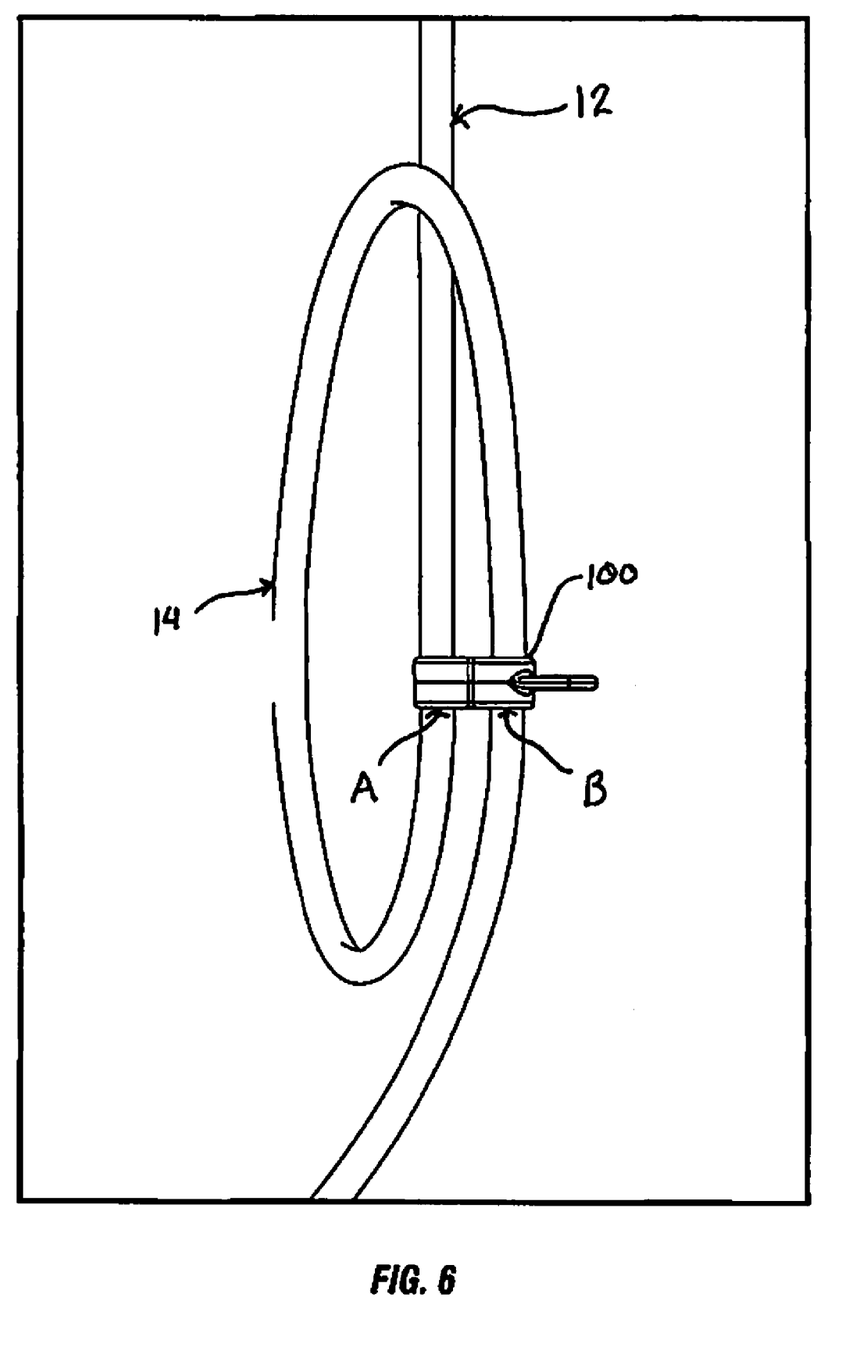
FIG. 6 is a side perspective view of the embodiment shown in FIGS. 4 and 5 employed to form an adjustable loop in a drain tube.

Referring now to FIG. 6, initially, adjustable loop 14 is formed using the excess length of drain tube 12. By slightly twisting and then overlapping two sections of drain tube 12, adjustable loop 14 may be formed in drain tube 12. The resulting adjacent sections of drain tube 12 are then inserted, one each, into recesses A, B of clip 100. The initial size of loop 14, and therefore, the effective length of drain tube 12, can be adjusted prior to inserting the respective section of drain tube 12 into recesses A, B of clip 100. In this configuration, a larger loop results in a shortened effective drain tube length, while a smaller loop causes the drain tube to have a longer effective length.

Figure 7:
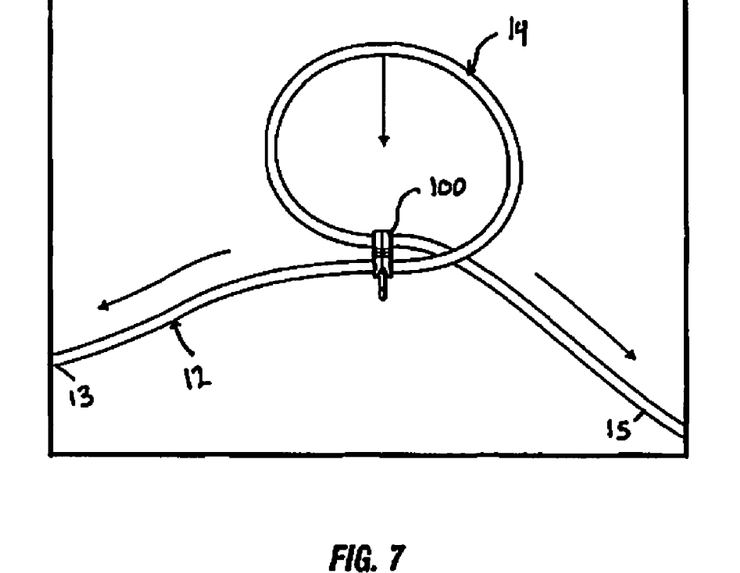
FIG. 7 is a top perspective view of the embodiment shown in FIG. 6 employed to form an adjustable loop in a drain tube, illustrating the process of lengthening the effective length of the drain tube.
Figure 8:
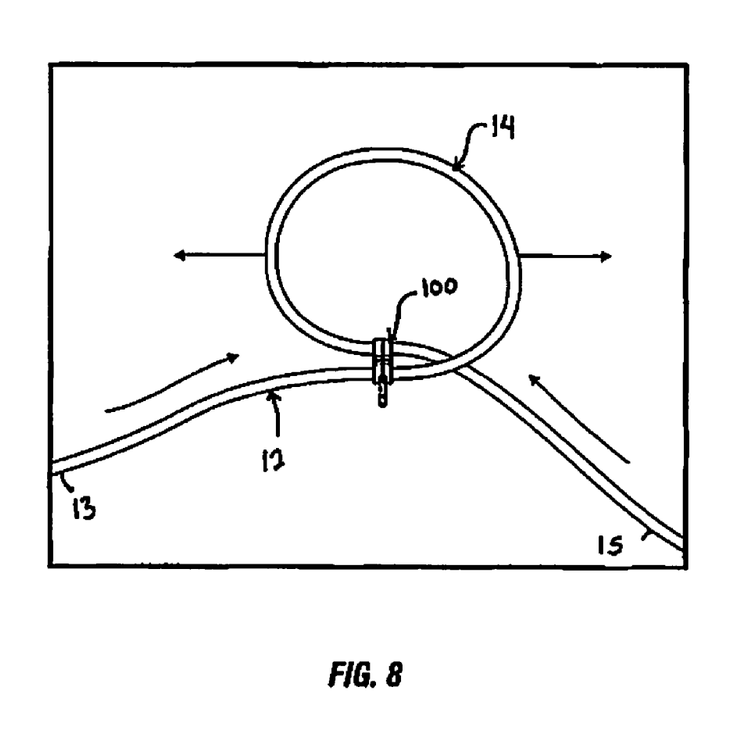
FIG. 8 is a top perspective view of the embodiment shown in FIG. 6 employed to form an adjustable loop in a drain tube, illustrating the process of shortening the effective length of the drain tube.

Referring now to FIGS. 7 and 8, the length of drain tube 12 can be adjusted by varying the dimension of adjustable loop 14 formed in drain tube 12. By reducing adjustable loop 14 in size the length of drain tube 12 can be increased (FIG. 7). Adjustable loop 14 in drain tube 12 is made smaller simply by disengaging the sections of drain tube 12 from within recesses A, B of clip 100 and pulling catheter end 13 and connector end 15 of drain tube 12 longitudinally in opposite directions. The resulting smaller loop formed in drain tube 12 can be maintained by reinserting adjacent sections of drain tube 12 into recesses A, B of clip 100. Adjustable loop 14 may be made larger by pushing catheter end 13 and connector end 15 of drain tube 12 longitudinally towards one another and extending the width of adjustable loop 14 (FIG. 8).

In an alternate means of adjusting the effective length of drain tube 12, instead of removing clip 100 from drain tube 12 to vary the dimension of loop 14, clip 100 may be configured to allow at least one section of drain tube 12 to be selectively positionable within at least one recess A, B. In this manner, neither section of drain tube 12 would need to be disengaged from clip 100 when varying the dimension of adjustable loop 14.

Clip 100 further includes fastener hoop 110 for assisting in securing loop 14 to a patient's bed or bed sheets. Fastener hoop 110 is integrally formed with base 102. Fastener hoop 110 may be used in combination with a fastening means, ie. safety pin, string, sheet tack or clip, to secure adjustable loop 14 above the horizontal plane defined by port 17 of fluid reservoir 16. As seen in FIGS. 2 and 3, sheet clip 101 is attached to fastener hoop 110 of clip 100, permitting adjustable loop 14 to be secured to the bed sheet or other object. Sheet clips and other fastening means are well known in the art and it is envisioned that fastener hoop 110 can be configured to securely engage any such known clips. In an alternate embodiment, clip 100 may instead include a sheet clip 101 integrally formed with base 102 of clip 100.

Figure 9:
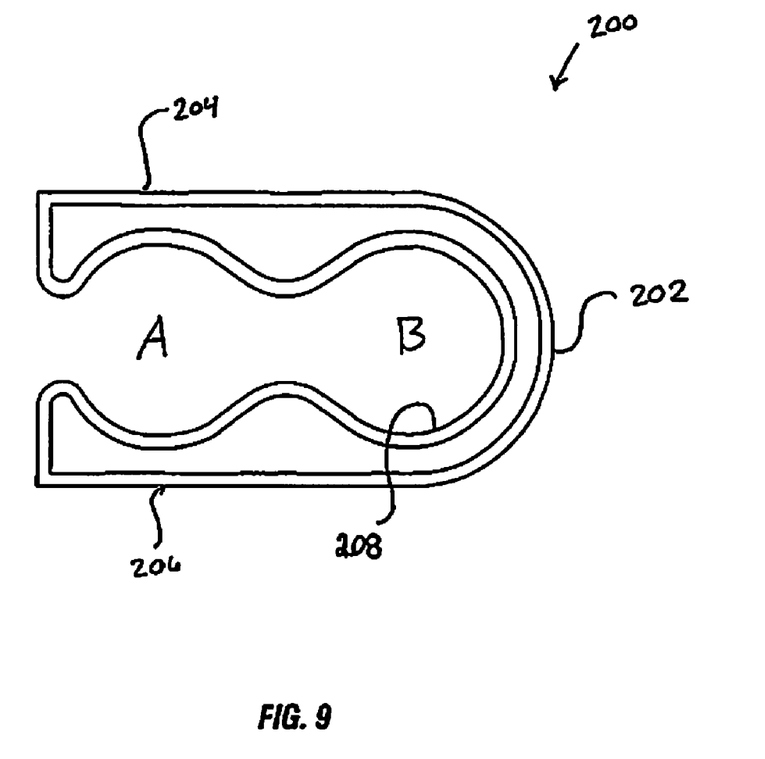
FIG. 9 is a side view of an alternate embodiment of a clip constructed in accordance with the present disclosure.
Figure 10:
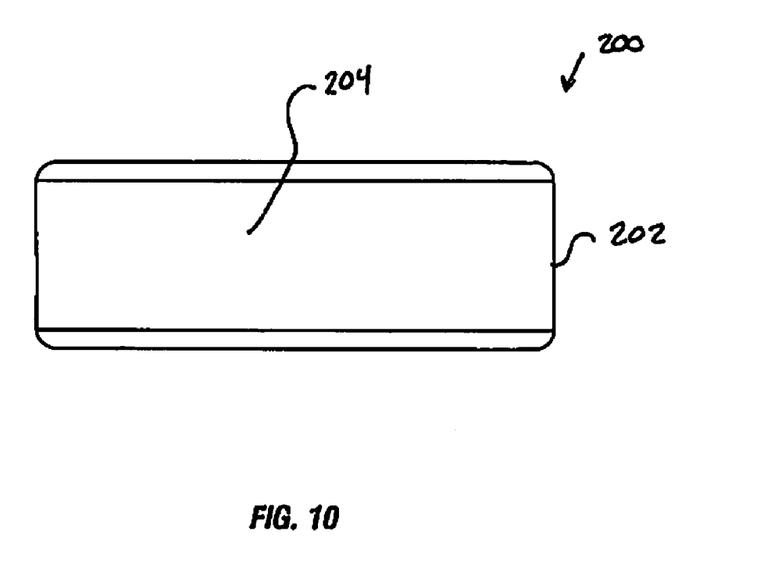
FIG. 10 is a top view of the embodiment shown in FIG. 9.

Turning now to FIGS. 9 and 10, an alternate embodiment of the present disclosure is generally designated as 200. Clip 200 is substantially similar to clip 100 and will only be discussed in detail to the extent necessary to identify differences in construction and operation.

As seen in FIGS. 9 and 10, clip 200 includes base 202 and longitudinally opposed arms 204 and 206 extending from base 202. Opposed arms 204, 206 are constructed and dimensioned to resiliently engage, grip and hold adjacent sections of drain tube 12 in juxtaposed or adjacent relationship to one another. Each of the opposed arms 204, 206 extend from base 202 in a mirror image relationship to one another to form an inner gripping surface 208. Gripping surface 208 defines recesses A and B configured for receiving sections of drain tube 12. Unlike clip 100, clip 200 does not include a fastener loop for securing drain tube 12 to the bed or bed sheets. Therefore, an additional fastener may be used in conjunction with drain tube 12 to secure adjustable loop 14 formed drain tube 12 to the bed or bed sheets.

Figure 11:
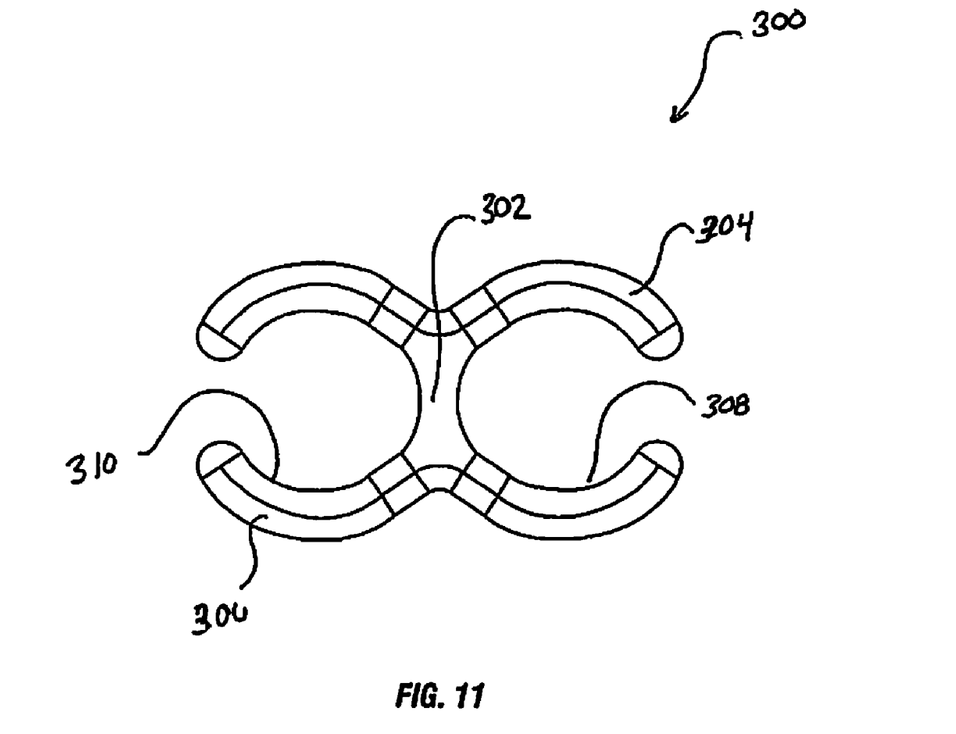
FIG. 11 is a side view of another embodiment of a clip constructed in accordance with the present disclosure.
Figure 12:
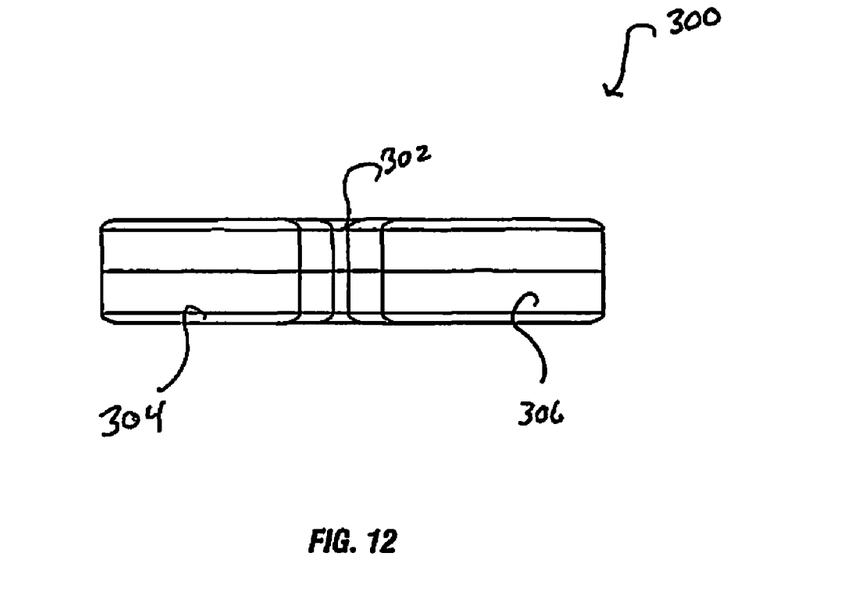
FIG. 12 is a top view of the embodiment shown in FIG. 11.

Turning now to FIGS. 11 and 12, an alternate embodiment of the present disclosure is generally designated as 300. Clip 300 is substantially similar to clip 200 and will only be discussed in detail to the extent necessary to identify differences in construction and operation.

As seen in FIGS. 11 and 12, clip 300 includes base 302 and opposed generally C-shaped arms 304 and 306 that are constructed and dimensioned to resiliently engage, grip and hold adjacent sections of drain tube 12 in juxtaposed or adjacent relationship to another. Each of the opposed generally C-shaped arms 304, 306 have a pair of opposed flexible curvilinear arms in mirror image relationship to one another to form an inner gripping surfaces 308, 310. As with clip 200 illustrated in FIGS. 9 and 10, clip 300 does not include a fastener for securing adjustable loop 14 of drain tube 12 to the bed or bed sheets. Therefore, an additional fastener must be included to secure drain tube 12 to the bed or bed sheets and to prevent adjustable tube 12 from falling below port 17 of fluid reservoir 16.

Figure 13:
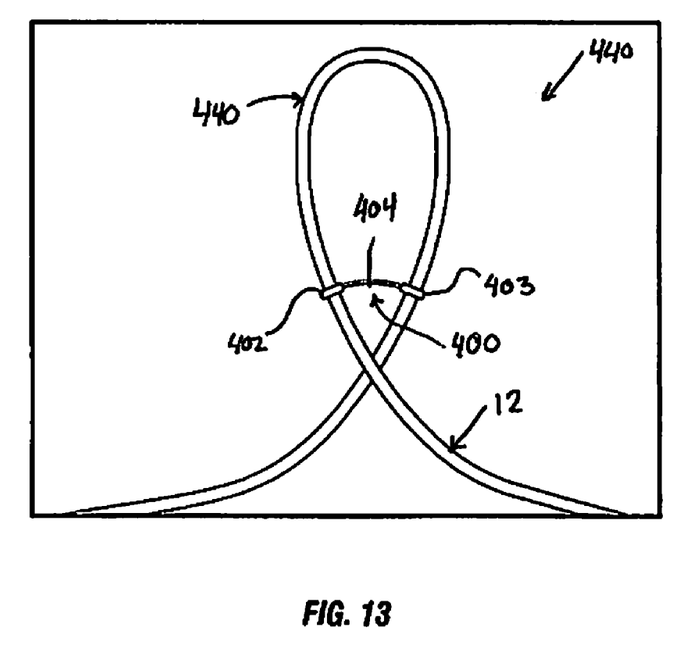
FIG. 13 is a side view of an embodiment of an adjustable drain tube loop constructed in accordance with the present.
Figure 14:
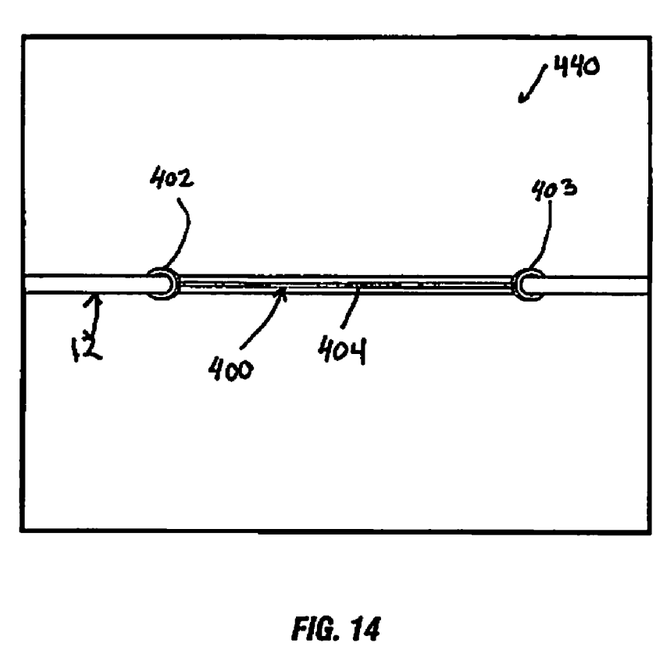
FIG. 14 is a side view of the embodiment shown in FIG. 13 wherein the adjustable loop has been completely distended.

Turning now to FIGS. 13 and 14, an adjustable drain tube loop constructed in accordance with the present disclosure is generally designated as 440. Adjustable drain tube loop 440 is maintained by flexible band 400. Flexible band 400 includes a pair of rings 402, 403 and a elastic cord 404 connecting rings 402, 403. Rings 402, 403 are sized to slideably engage drain tube 12 while in a relaxed position (FIG. 13). In the event the effective length of drain tube 12 must be increased, flexible band 400 permits limited movement while in a relaxed position. Flexible band 400, however, may be stretched to extend drain tube 12 to its original, unlooped length (FIG. 14). In this manner, while elastic cord 404 is stretched to extend drain tube 12, rings 402, 403 are also acted upon by the stretching force applied by elastic cord 404 and become slightly deformed. This deformation permits rings 402, 403 to grip drain tube 12 and prevent flexible band 400 from sliding and returning to a relaxed position. Once the force applied to stretch elastic cord 404 is remove, adjustable loop 440 returns to drain tube 12.

Figure 15:
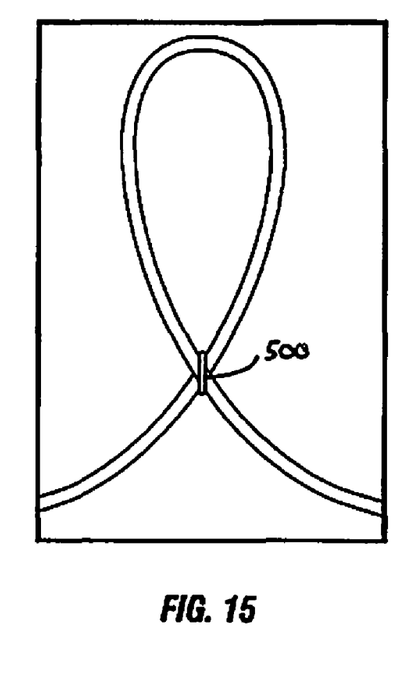
FIG. 15 is a side view of an alternate embodiment of an adjustable drain tube loop constructed in accordance with the present disclosure.
Figures 16, 17:
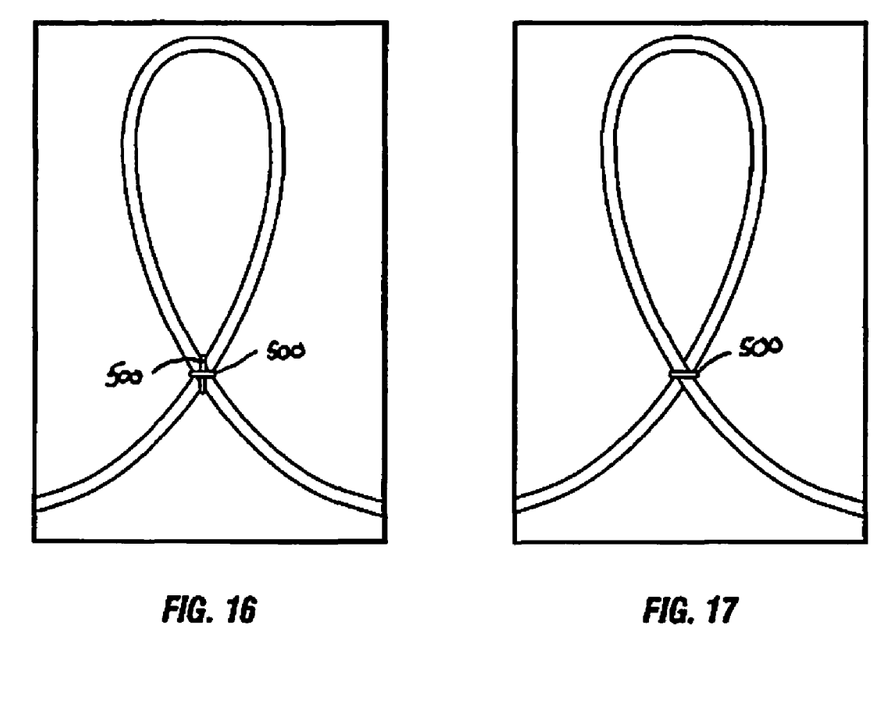
FIG. 16 is a side view of another alternate embodiment of an adjustable drain tube loop constructed in accordance with the present disclosure.
FIG. 17 is a side view of yet another alternate embodiment of an adjustable drain tube loop constructed in accordance with the present disclosure.

Turning now to FIGS. 15-17, alternate configurations of adjustable drain tube loops constructed in accordance with the present disclosure are shown. FIGS. 15-17 include one or more bands, 500 for maintaining an adjustable drain tube loop in drain tube 12. Band or bands 500 may be positioned around the intersecting section of drain tube 12 in a horizontal orientation (FIG. 17), in a vertical orientation (FIG. 16), or both in horizontal and vertical orientations (FIG. 15). Band 500 may be constructed of any material, including plastic, rubber, cloth and metal. Band 500 may be constructed of a single strand or multiple strands of material. Band 500 is sized to slideably engage drain tube 12. Band 500 may be releasably engageable with drain tube 12. The effective length of drain tube 12 can be adjusted by varying the size of the adjustable tube 12 as described above with respect to the alternate embodiments. As with the other embodiments for maintaining the adjustable loop without a fastener loop, the adjustable drain tube loop shown in FIGS. 15-17 must also include a sheet clip or other fastener for attaching drain tube 12 to the bed or bed sheets. In an alternate embodiment, band 500 may include a fastening means for attaching drain tube 12 with the bed or bed sheets.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. A method of preventing back pressure in a drain tube of a urine collection/monitoring system, the method comprising the steps of:
   providing a drain tube having a first end communicating with a catheter and a second end communicating with a fluid reservoir, wherein the catheter is configured to be received within a bladder of a patient;
   forming a loop in the drain tube between the patient and the fluid reservoir;
   securing the loop in the drain tube using a clip, wherein the clip secures first and second overlapping sections of the drain tube such that each of the overlapping sections is slidably repositionable in relation to the clip;
   positioning the loop horizontally above a collection/monitoring device of the collection/monitoring system; and
   repositioning at least one of the overlapping sections in relation to the clip to adjust a diameter of the loop to prevent the drain tube from falling below an inlet port of the fluid reservoir.

2. The method of claim 1, wherein the clip includes a pair of spaced apart arms for adjustably retaining first and second sections of the drain tube.

3. The method of claim 1, further including the step of securing the loop to a bed.

4. The method of claim 3, wherein the loop is secured to the bed using a sheet clip.

5. The method of claim 1, wherein the step of positioning the loop horizontally above the collection/monitoring device includes placing the loop on a bed of a patient.

6. The method of claim 1, wherein the clip includes a pair of spaced arms extending from a base, the arms forming an inner gripping surface defining first and second recesses, wherein the inner gripping surface is configured to retain, while simultaneously allowing for adjustment of, a first section of drain tube within the first recess and a second section of drain tube within the second recess.

* * * * *